(12) United States Patent
Bouamrani et al.

(10) Patent No.: US 10,149,668 B2
(45) Date of Patent: Dec. 11, 2018

(54) DEVICE FOR IN VIVO SAMPLING OF BIOLOGICAL SPECIES

(71) Applicant: COMMISSARIAT A L'ENERGIE ATOMIQUE ET AUX ENERGIES ALTERNATIVES, Paris (FR)

(72) Inventors: Mohamed-Ali Bouamrani, Grenoble (FR); François Berger, Meylan (FR); Matthieu Dreyfus, Grenoble (FR); Adrien Mombrun, Grenoble (FR)

(73) Assignee: COMMISSARIAT A L'ENERGIE ATOMIQUE ET AUX ENERGIES ALTERNATIVES (FR)

( * ) Notice: Subject to any disclaimer, the term of this patent is extended or adjusted under 35 U.S.C. 154(b) by 372 days.

(21) Appl. No.: 14/901,231

(22) PCT Filed: Jun. 30, 2014

(86) PCT No.: PCT/EP2014/063806
§ 371 (c)(1),
(2) Date: Dec. 28, 2015

(87) PCT Pub. No.: WO2014/207254
PCT Pub. Date: Dec. 31, 2014

(65) Prior Publication Data
US 2016/0296215 A1    Oct. 13, 2016

(30) Foreign Application Priority Data

Jun. 28, 2013    (FR) ...................................... 13 56289

(51) Int. Cl.
*A61B 5/00*    (2006.01)
*A61B 10/04*    (2006.01)
(Continued)

(52) U.S. Cl.
CPC .............. *A61B 10/04* (2013.01); *A61B 10/02* (2013.01); *A61F 13/38* (2013.01);
(Continued)

(58) Field of Classification Search
CPC ..... A61B 10/02; A61B 10/04; A61B 10/0045; A61B 10/0051; A61B 2010/0216
(Continued)

(56) References Cited

U.S. PATENT DOCUMENTS 6,194,199 B1 *    2/2001    Asa ........................ C12M 23/08
                                                     15/236.01
6,755,837 B2 *    6/2004    Ebner ................ A61B 17/1635
                                                     600/570
(Continued)

FOREIGN PATENT DOCUMENTS

EP          0277009 A2    8/1988
WO       0197693 A1    12/2001
(Continued)

OTHER PUBLICATIONS

International Search Report and Written Opinion for Application No. PCT/EP2014/063806 dated Sep. 12, 2014.

*Primary Examiner* — Max Hindenburg
(74) *Attorney, Agent, or Firm* — Lerner, David, Littenberg, Krumholz & Mentlik, LLP

(57) ABSTRACT

The invention relates to a device for in vivo sampling of biological species, comprising:—a capture medium made from a nanoporous material, having a capture surface for said species, said capture medium being supported by a plate,—a gripping rod,—an articulation comprising a first limb coupled to the gripping rod and a second limb coupled removably to the plate supporting the capture medium, such that the capture surface can be selectively oriented relative
(Continued)

Figure 1:
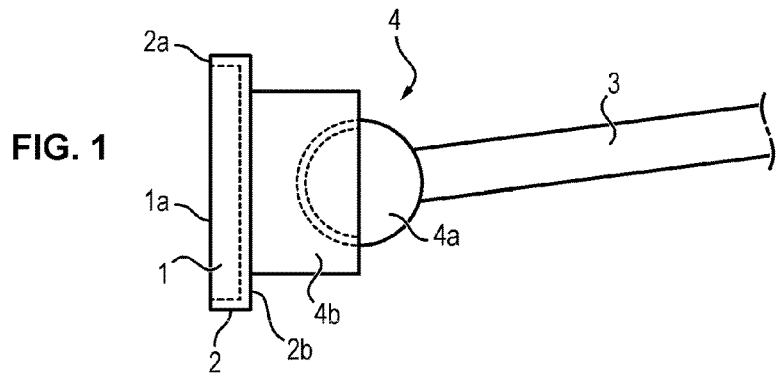

to the gripping rod, so as to adjust the orientation of the capture medium relative to the gripping rod.

11 Claims, 4 Drawing Sheets

(51) Int. Cl.
*A61B 10/02* (2006.01)
*A61F 13/38* (2006.01)
*A61B 17/00* (2006.01)
*A61F 13/53* (2006.01)

(52) U.S. Cl.
CPC ............... *A61B 2010/0216* (2013.01); *A61B 2017/00358* (2013.01); *A61F 2013/53081* (2013.01)

(58) Field of Classification Search
USPC ........................................................ 600/572
See application file for complete search history.

(56) References Cited

U.S. PATENT DOCUMENTS

| | | | |
|---|---|---|---|
| 7,037,307 B2* | 5/2006 | Dennis | A61B 18/14 606/110 |
| 8,152,736 B2* | 4/2012 | Caillat | A61B 10/02 600/562 |
| 8,641,642 B2* | 2/2014 | Giddings | A61B 10/0051 600/570 |
| 8,753,897 B2* | 6/2014 | Ferrari | B01D 15/00 250/288 |
| 8,998,824 B2* | 4/2015 | Pierce | A61B 10/0045 600/572 |
| 9,072,499 B2* | 7/2015 | Birnboim | A61B 10/0045 |
| 9,204,865 B2* | 12/2015 | Polzius | A61B 10/0051 |
| 2005/0010095 A1 | 1/2005 | Stewart et al. | |
| 2009/0317835 A1 | 12/2009 | Cosnier et al. | |
| 2013/0079663 A1 | 3/2013 | Caillat et al. | |

FOREIGN PATENT DOCUMENTS

| | | |
|---|---|---|
| WO | 2006082344 A1 | 8/2006 |
| WO | 2011090778 A1 | 7/2011 |

* cited by examiner

DEVICE FOR IN VIVO SAMPLING OF BIOLOGICAL SPECIES

CROSS REFERENCE TO RELATED APPLICATIONS

The present application is a national phase entry under 35 U.S.C. § 371 of International Application No. PCT/EP 2014/063806, filed Jun 30, 2014, published in French, which claims priority from French Patent Application No. 1356289, filed Jun 28, 2013, the disclosures of which are incorporated by reference herein.

FIELD OF THE INVENTION

The present invention relates to a device for in vivo sampling of biological species.

BACKGROUND OF THE INVENTION

Tissue analysis is the best indicator for accessing relevant biological information directly from a pathological source.

Micro-invasive exploration is mainly based on puncture biopsy, which may be performed via a first endoscopic or laparoscopic route.

Many miniaturized devices have thus been developed for attaining deep organs and the target tissue by passing in an atraumatic way through natural routes, like the digestive tract, the cardiovascular system, the urinary system or the respiratory system.

These biopsies, however, cause a haemorrhagic or infectious risk which is not negligible because of the produced tissue lesions.

Consequently, many pathological territories, such as the peri-tumoral region left in place by the surgeon therefore remain inaccessible.

Further, the significant mutational polymorphism requires extensive sampling of the tumour, incompatible with micro-invasive biopsy approaches.

On the other hand, because of their cost and of the time required for their application, present procedures are difficult to be compatible with the need of having available extemporaneous analyses, i.e. achieved on the operating theatre during a surgical operation, in order to assist with the decisions of the surgeon.

The object of the invention is to remedy the drawbacks of the existing devices and to allow a collection of pathological molecules but also of cells which does not cause lesion of the tissues and which is further compatible with extemporaneous analyses.

SUMMARY OF THE INVENTION

According to the invention, a device for in vivo sampling of biological species is proposed, comprising:
- a capturing support in a nanoporous material, having a surface for capturing said species, said capturing support being borne by a plate,
- a grasping rod,
- a joint comprising a first member coupled with the grasping rod and a second member coupled removably with the plate bearing the capturing support, so that the capture surface is selectively orientable with respect to the grasping rod, so as to adjust the orientation of the capturing surface with respect to the grasping rod.

By "nanoporous material" is meant a crystalline or amorphous material in one piece and preferably of homogenous composition, having pores for which the average diameter is less than one micrometer and in particular less than or equal to 100 nm. Among nanoporous materials, microporous materials, (pores with an average diameter comprised between 0.2 and 2 nm), mesoporous materials (pores with an average diameter comprised between 2 and 50 nm) and macroporous materials (pores with an average diameter comprised between 50 and 1000 nm) are notably distinguished.

Preferably, the porosity of said material, i.e. the ratio between the volume of the pores and the total volume of the material, is greater than or equal to 10%.

Biological species which may be adsorbed on said nanoporous material may be cells (for which the diameter is comprised between about 1 $\mu$m and 50 $\mu$m), bacteria, viruses, circulating vesicles like exosomas (diameter comprised between about 20 and 200 nm), but also molecules or macromolecules, such as proteins (diameter comprised between a few nanometers and a few tens of nanometers), peptides (size of the order of one nanometer), metabolites. The "size" of these molecules is meant as their largest dimension.

The device according to the invention gives the possibility of doing without the sampling of a tissue fragment by capturing biological species by simple contact between the nanoporous capture surface and the tissue of interest.

Said device therefore gives the possibility of producing a molecular or cell imprint being integrated to endoscopic or laparoscopic explorations, notably during the exploratory approach of non-biopsiable tissues or organs.

Indeed, the nanoporous capture surface has the capacity, in contact with living tissue, of capturing a layer of surface cells, in a non-lesional way, while retaining the histological structure of the targeted tissue. Said surface further gives the possibility of retaining the molecular species present in the interstitial liquid of the tissue.

On the other hand, the biological material captured on the nanoporous surface may be directly analysed by means of conventional histological techniques (staining, immuno-marking), but also by mass spectrometry MALDI (imaging and/or profiling). By "directly", is meant that the analysis is directly carried out on the biological material present on the capturing support, without separating it from said support.

In a particular advantageous way, the first and second members of the joint may be separated so as to detach the capture support from the grasping rod.

Preferably, the capture support is fitted into the plate, said plate having a rim flush with the capture surface, so that only the capture surface of said support is in contact with tissues during in vivo sampling.

Preferably, the plate is in an electrically conducting material, which allows it to be maintained secured to the capture support for analyses of the MALDI type.

According to an embodiment, the joint is a ball joint.

According to an embodiment of the invention, the material of the capture support is nanoporous silicon.

Advantageously, the capture surface is included in a circle with a diameter of less than 10 mm.

The device may further comprise a device for orienting the capture support, comprising a cable extending along the grasping rod and coupled with the second member of the joint.

Such a device advantageously gives the possibility of applying an automated method for analysis of biological species captured by means of such a device, comprising:

providing a plurality of capture supports comprising biological species adsorbed on the capture surface of each support, providing a measurement support having the shape of an electrically conducting plate comprising a plurality of housings, the shape and the dimensions of which are adapted to those of the capture supports in order to allow electric contact between the measurement support and each capture support, setting into place each capture support in a corresponding housing of the measurement support, automatically depositing an organic matrix on each capture surface, automatically acquiring mass spectrometry measurements on each capture surface.

According to an embodiment of the invention, the plate in which is fitted the capture support is electrically conducting, said plate having a rim flush with the capture surface, and the capture support and the plate in which it is fitted is set into place into each housing of the measurement support.

According to a particular embodiment, the measurement support comprises 96 housings for capture supports.

SHORT DESCRIPTION OF THE DRAWINGS

Figure 2A:
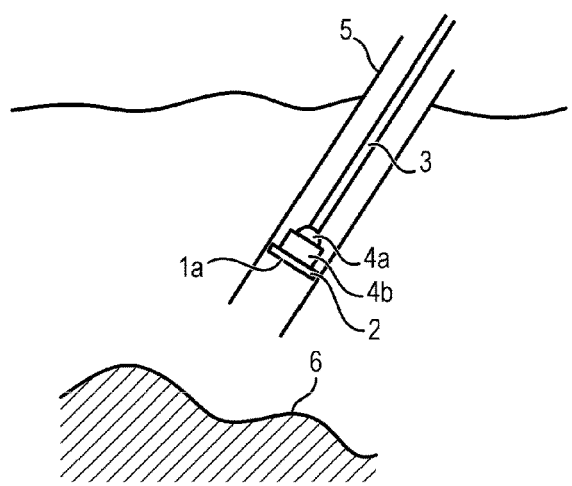
Figure 2B:
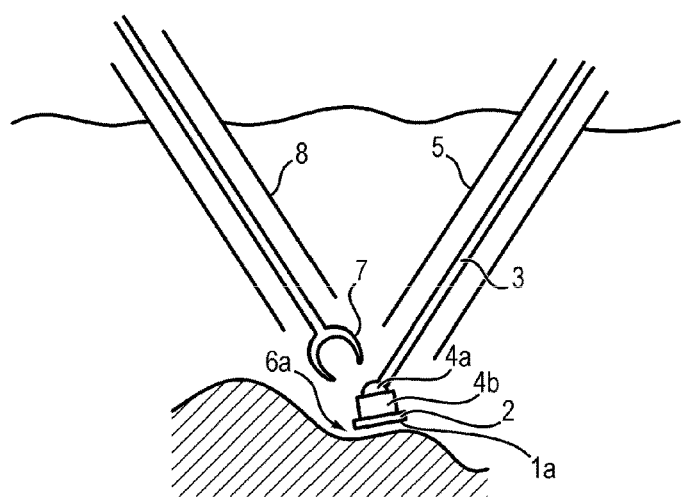
Figure 2C:
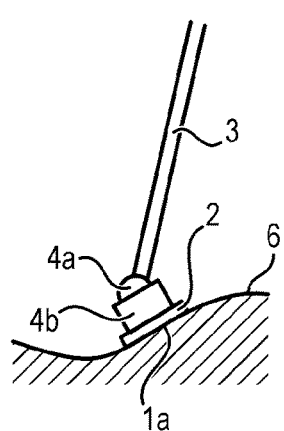
Figure 2D:
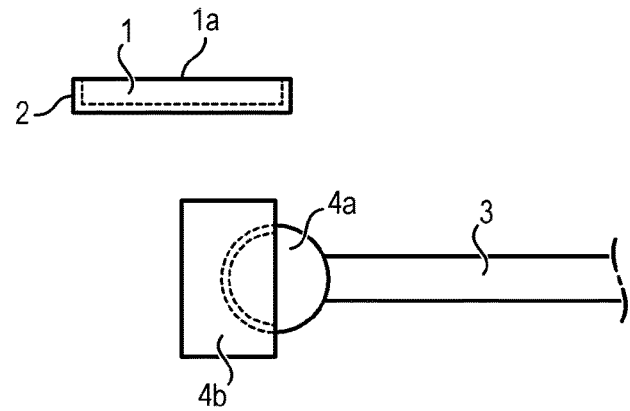
Figure 3A:
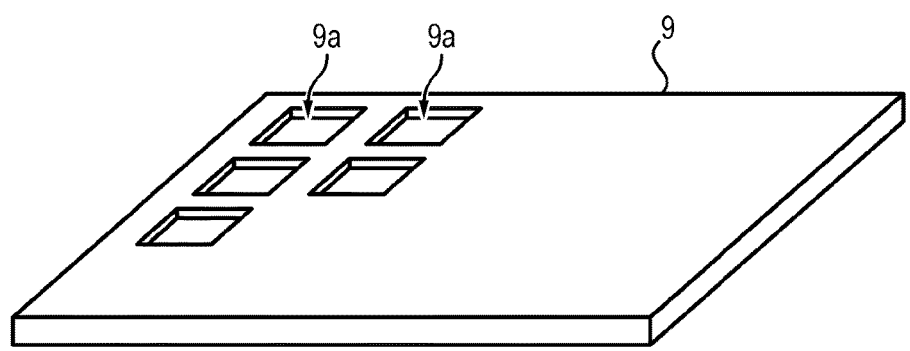
Figure 3B:
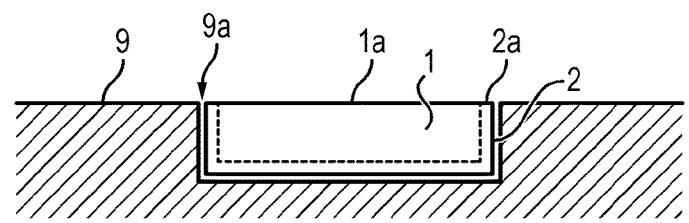
Figure 4:
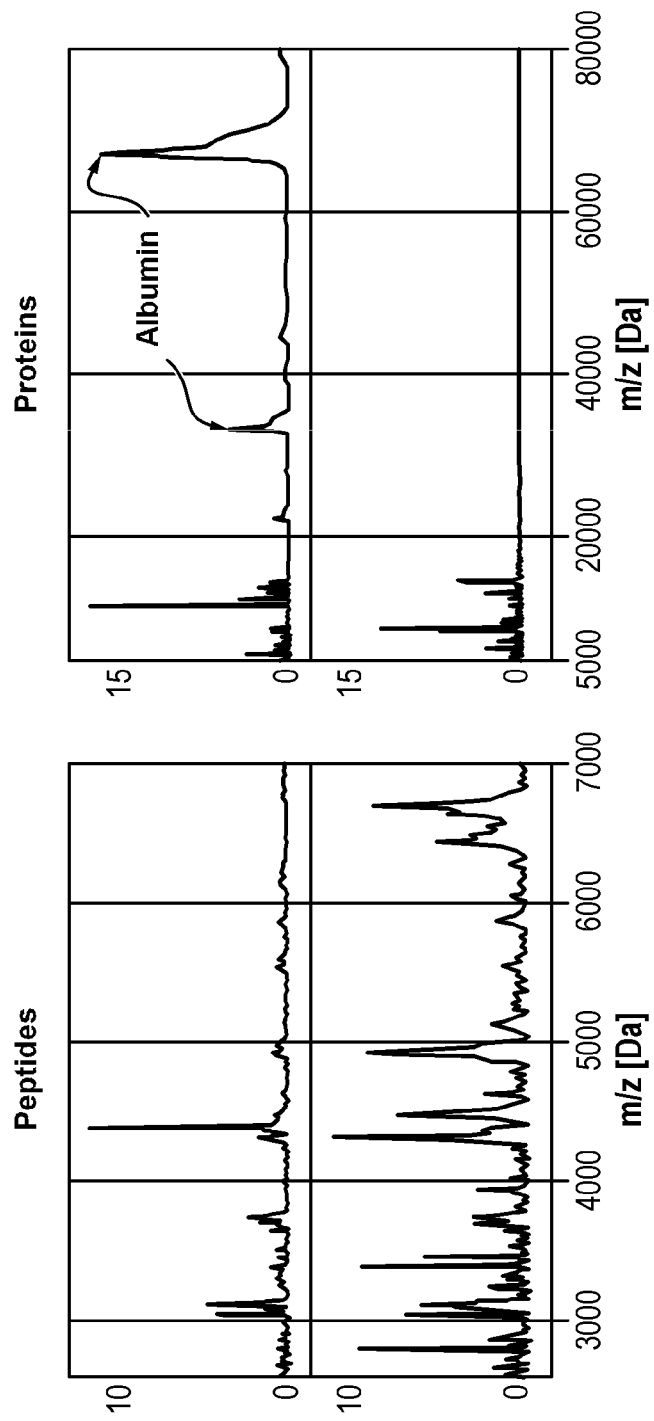
Figure 5:
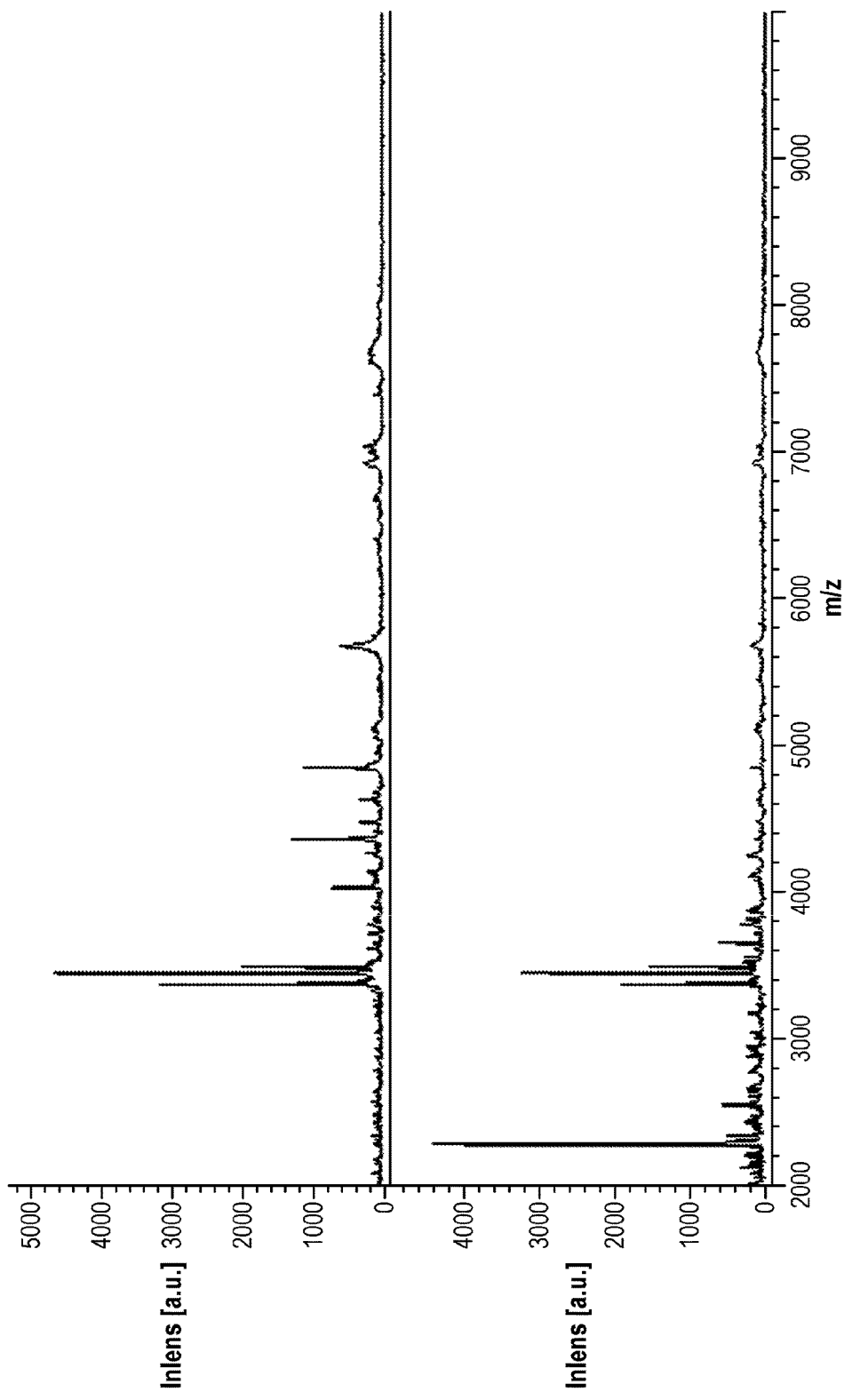

Other features and advantages of the invention will become apparent from the description which follows, with reference to the appended drawings wherein:

FIG. 1 is a block diagram of a sampling device according to an embodiment of the invention, FIGS. 2A to 2D schematically illustrate different steps of the use of such a sampling device, FIG. 3A is a perspective view of a measurement support for automated analysis of a plurality of capture supports; FIG. 3B is a sectional view of a housing of such a support in which are laid out a capture support and the plate into which it is fitted, FIG. 4 shows mass spectra of proteins and peptides of human cerebrospinal liquid captured by means of a capture support in nanoporous silicon and a smooth reference support, FIG. 5 shows mass spectra obtained for two areas of a same prostate resulting from surgical excision.

DETAILED DESCRIPTION OF THE INVENTION

FIG. 1 schematically illustrates a sampling device according to an embodiment of the invention.

Said device comprises a capture support 1, one surface of which is intended to form the capture surface 1a for the biological species to be sampled.

The capture surface 1a may have a rectangular, circular shape or any other shape.

The capture surface 1a is generally planar.

Preferably, the capture surface 1a is included in a circle with a diameter of less than 10 mm, so as to be able to be inserted, depending on the case, in a colonoscopy trocar or an operator channel of conventional endoscopy so as to be brought as far as the tissues in which taking a sample is desired.

The largest dimension of the capture surface 1a is generally greater than the thickness of the support 1.

Purely as an indication, the capture surface may be a square with a side of 5 mm, while the thickness of the capture support may be comprised between 100 μm and 2 mm, for example of the order of 750 μm.

The capturing support 1 is in a nanoporous material.

According to a preferred embodiment, the nanoporous material is nanoporous silicon.

Advantageously, said nanoporous silicon may have at least one of the following properties, and preferably the whole of these properties:

pores with a dendritic structure, pores with an average diameter comprised between 1 and 100 nm, a porosity comprised between 40% and 65% over a depth comprised between 10 nm and 100 μm.

An advantage of nanoporous silicon is that it does not require functionalization of the capture surface for adsorbing biological species.

Another advantage of nanoporous silicon is that it supports sterilization treatments conventionally applied to surgical instruments, in particular with an autoclave.

Nanoporous silicon (and more particularly mesoporous silicon) may be obtained by electrochemical anodization of p+ doped silicon with a conductivity of 10 to 20 mΩ·cm in a hydrofluoric acid solution (HF) at about 15%. To do this, the material is soaked in an HF bath and subject to electrolysis, this method being known per se. In this way a material is obtained having a porosity of dendritic structure; this means that the pores do not have a rectilinear axis and that they extend into the depth of the material along a discontinuous direction and may cross each other. This dendritic structure promotes suction. The porosity is comprised between 40 and 65%. The porosity extends over a depth of about 6 μm; beyond, massive silicon is again found. Generally, for a capture support which may be used in the invention, the porosity of the material extends over a depth which may be comprised between 10 nm and 100 μm.

Naturally, this is a porous surface of said material which is used as a capture surface.

By varying the manufacturing parameters (HF concentration, anodization time, current density, type of silicon), it is possible to vary the characteristics of the nanoporous silicon.

Alternatively, it is possible to manufacture nanoporous silicon having an ordered structure by means of an electron-beam lithography process.

Naturally, any other method for obtaining nanoporous silicon may be used without however leaving the scope of the present invention.

On the other hand, the invention is not limited to nanoporous silicon and one skilled in the art may also select another nanoporous material, for example a block copolymer, a material of the sol-gel type, a material of the SiOCH type which has been made porous. Such materials are notably made porous by resorting to pore-forming agents, according to known methods.

Advantageously, the capture support 1 is borne by a plate 2.

Preferably, said plate 2 has a housing for the support, said housing being delimited by a rim 2a, the height of which is substantially equal to the thickness of the support 1.

Thus, the capture surface 1a is flush with the rim 2a of the plate, so that only the capture surface 1a is in contact with the tissues during the sampling.

Thus, it is avoided that the edges of the capture support, which may be sharp, damage the tissues.

Moreover, the outer shapes of the plate 2 are designed so as not to be aggressive for the tissues; in particular, they preferably do not have any sharp angle.

The outer dimensions of the plate 2 are preferably as reduced as possible, so as to facilitate its insertion as far as the sampling site.

The plate is advantageously in metal; as this will be seen below, the fact that the plate is electrically conducting gives the possibility of retaining the capture support 1 in the plate 2 for mass spectrometry analyses.

However, as this embodiment is not limiting, it is possible to select for the plate 2 any other suitable material which may be sterilized.

The capturing support 1 is maintained in its housing by any means either removable or not.

Said means may comprise an adhesive, notably a biocompatible adhesive, a snap-on fastening, etc.

Advantageously, the plate may have a parallelepipedal or cylindrical shape, which facilitates its use when it is intended to maintain the capture support during subsequent analyses.

In particular, if the plate 2 has a flat bottom 2b, it may be laid in a stable way on a table and put into contact with a planar measurement support.

The sampling device further comprises a grasping rod 3 allowing handling of the capture support 1 upon its introduction into the body and sampling on the tissues of interest.

If the tissues are approached by laparoscopy, the rod 3 is rigid, which facilitates its insertion through a trocar.

If the tissues are approached by endoscopy, the rod 3 is flexible, so as to be able to take operative channels.

The person skilled in the art is able to select the suitable material for the rod 3 depending on the intended application, by taking into account constraints related to the sterilization of the device.

The diameter of the rod is adapted for passing through a trocar or an operative channel for endoscopy.

The length of the rod 3 is variable depending on the contemplated handling method.

If the rod is intended to be handled from the outside of the body, its length is greater than the distance between the tissues of interest and the outside of the body.

The rod may then have a length of a few tens of centimeters.

Optionally, the rod may be telescopic.

The rod may on the other hand be shorter if it is borne by a clamp or a robot as far as the sampling site; in this case, a length of a few centimeters is sufficient.

The capture surface 1a may be oriented relatively to the rod 3 via a joint 4.

Preferably, said joint is a ball joint, since it allows a greater number of degrees of freedom for tilting the capture surface.

It is however possible to select another joint, for example a hinge.

The joint 4 comprises a first member 4a coupled with the rod 3 and a second member 4b coupled with the plate bearing the capture support, the first and the second member being orientable relatively to each other.

If the joint is a ball joint, the first member is a ball and the second member is a cup having a spherical housing for the ball, or vice versa.

Optionally, the first and second members may be separated from each other, for example by giving them sufficient elasticity for allowing one or several sequences of snap-on fastening and snap-off unfastening.

The person skilled in the art selects a suitable material for both members of the joint, notably by taking into account sterilization and optionally disassembling constraints.

The first member 4a is coupled with the rod 3 by any suitable, removable means or not.

Said first member 4a is for example stuck at the end of the rod 3, notably by means of a biocompatible adhesive.

Alternatively, the first member 4a may be an integral part of the rod 3, i.e. manufactured in a single part with the latter.

The second member 4b of the joint is removably coupled with the plate 2.

The connection between the plate 2 and the second member 4b may thus be disassembled, for example by snap-on fastening, screwing, etc.

In this case, it is not necessary that the actual joint 4 be able to be disassembled.

By being able to separate the plate 2 bearing the capture support 1 of the rod 3 (either by detaching both members 4a, 4b of the joint, or by detaching the plate 2 from the second member 4b of the joint) it is possible to replace a support already used with a new support, borne by a new plate.

Thus it is possible to successively perform samplings on a same site by using the same rod and by successively attaching thereto several capture supports.

The design allowing detachment of the plate 2 from the assembly consisting of the rod 3 and of the two members 4a, 4b of the joint is preferable since it gives the possibility of retaining the most complex mechanism for its reuse and for simply replacing the plate, the geometry of which is generally simpler and is less costly.

Preferably, a connection between the plate 2 and the second member 4b of the joint, which is easy and rapid to disassemble, preferably without requiring any tools, is selected.

Naturally, for safety reasons, any connection which may be disassembled in the sampling device should be sufficiently strong in order to avoid any untimely detachment of an element relatively to the remainder of the device, notably when the latter is inside the body.

Preferably, the connections which may be disassembled are made by sufficiently rigid snap-on fastening so as to be suitably secured to the remainder of the device.

According to an embodiment (not shown), the capture surface 1a may be oriented by a user from the outside.

The sampling device for this purpose comprises an orientation device connected to the second member of the joint and which may be actuated from the outside.

For example, said orientation device comprises a cable attached to the second member of the joint and extending along the grasping rod 3.

An operating mode of the sampling device will now be described, with reference to FIGS. 2A to 2D.

Generally, the device may be used for sampling biological species in any organ or tissue approached by endoscopy or colonoscopy.

For example, and in a non-limiting way, said device may be used for samples taken in the prostate, in the bladder, in the stomach, etc.

Once the capture support is connected to the end of the grasping rod via the joint, the device is introduced into a trocar or into an operative endoscopy channel 5 (FIG. 2A).

If the grasping rod is not sufficiently long so as to be directly handled by the user from the outside, it is held by a clamp manually actuated or by a robot (not shown).

The trocar or the operative channel 5 protects the capture surface 1a during its insertion and during its withdrawal.

It is therefore not necessary to provide the sampling device with a specific protection of the capture surface.

When the capture support 1 is found at the tissue 6 in which samplings are intended to be made, the orientation of the capture surface 1a is adjusted so as to make it substantially parallel to the surface 6a of the tissue in the sampling area (FIG. 2B), and then the capture surface is applied against the tissue, like a swab (FIG. 2C).

It is no longer necessary for this purpose to exert pressure on the capture support, contact being sufficient for allowing capture of the biological species.

The capture surface in a nanoporous material is smooth to the touch and does not exhibit any significant roughness, which minimizes the risks of lesion of the tissues.

The sampling of the biological species is therefore not performed by micro-abrasion nor by chemical functionalization but by a suction effect due to the nanopores.

This effect leads to preferential attachment of the peptides and of "small" molecules, having a size of the order of about 1 to 5 nm and/or a mass comprised between about 200 and 20,000 Da.

This property is advantageous since these small molecules are generally more useful as markers than molecules of larger dimensions.

The suction effect also explains the adhesion of the cells, which are too large for penetrating into the pores.

In terms of use, the handling of the device is different from a biopsy device as described in document WO 2006/082344, in which the capture surface is laid out on a portion of the rod while extending in a plane parallel to the longitudinal axis of the rod.

Indeed, in this known device, the gesture of the user consists of handling the rod tangentially to the tissue in which sampling is intended to be made, so as to affix thereon the capture surface.

This requirement of a tangential approach of the rod may pose problems of accessibility towards certain organs, the length of the rod being able to prevent access to regions of small dimensions.

On the contrary, with an orientable device according to the invention, the user handles the rod in a direction which is not necessarily tangential to the tissue but which may be tilted relatively to the latter, by orienting the capture surface so that it comes into contact with the tissue parallel to the latter.

By means of this possibility of selectively orienting only the capture support 1a and the second member 4b of the joint, which have reduced dimensions, as compared with the rod 3, it is possible to more easily access the tissues of interest, even when the sampling area is of small dimensions. By "selectively", is meant that the orientation of the capture surface may be adjusted with respect to the grasping rod.

As indicated above, the orientation of the capture surface 1a relatively to the rod may be achieved by an orientation device incorporated to the sampling device.

For example, if this is a cable, traction by the user gives the possibility of varying the tilt of the second member of the joint relatively to the first one.

However, the sampling device may also be passive, i.e. not comprise itself any means allowing adjustment of the orientation of the capture surface from the outside.

In this case, and as illustrated in FIG. 2B, the orientation of the capture surface 1a is achieved by handling the second member 4b of the joint by means of a clamp 7 introduced at the sampling site by another trocar or operative channel 8, said clamp 7 being handled by the other hand of the user, by another user or by a robot, until the capture surface 1a is adequately oriented relatively to the tissue 6.

Once the sampling has been carried out, the user withdraws the sampling device with the trocar or the operative channel through which it was introduced.

With view to analysing the captured species, the capture support 1a (possibly secured to the plate 2 and/or to the second member of the joint) is separated from the remainder of the sampling device (cf. FIG. 2D).

If other samplings have to be made, it is sufficient to put back into place a virgin capture support (optionally secured to a new plate and/or a new second member of the joint) for a new sampling.

A rinsing of the capture support gives the possibility of removing the species which would not have been adsorbed on the capture surface and/or impurities which would be deposited on the latter.

The biological species captured in the capture support are then analysed.

Preferably, this analysis is carried out extemporaneously, i.e. at the operating theatre, in order to rapidly shed light on the surgeon on the continuation of the surgical operation.

For example, in the case of prostatectomy, the surgeon makes tissue imprints at the region which he/she has already removed, and the result of the analyses allows him to determine if cancer tissues subsist, to be removed or if he/she may stop the intervention.

This gives the possibility of avoiding the removal of more tissues than required and thus minimizes the risks of sequelae (incontinence, impotence) for the patient.

In a particularly advantageous way, the capture support may be directly used for carrying out these analyses, without it being necessary to desorb the species of the nanoporous material in order to separate them from it.

Thus, the capture support, optionally secured to the plate, may be introduced into a measurement apparatus adapted for analysing the captured species.

Typically, the analyses may be achieved by mass spectrometry with laser desorption, of the MALDI or SELDI type.

The obtained protein profile is actually specific to the pathological nature or not of the studied tissue and is an addition to the clinical histological analysis.

For applying mass spectrometry directly on the capture support, the nanoporous material should preferably be electrically conducting, which is the case of nanoporous silicon.

Alternatively, if the nanoporous material is not electrically conducting, the capture support should be sufficiently thin for allowing analysis of the MALDI or SELDI type. In such a case, it is deposited on an electrically conducting material.

Advantageously, if the plate is also electrically conducting, the capture support may be maintained in the plate and the assembly is introduced into the mass spectrometer.

First, a suitable organic matrix is deposited on the capture surface, which co-crystallizes with the adsorbed species and then allows their desorption with the laser.

As this technique is known to the person skilled in the art, it will not be described in detail herein.

According to a particularly advantageous embodiment, it is possible to analyse in an automated way a plurality of capture supports.

For this purpose, as illustrated in FIG. 3A, the invention proposes a measurement support 9, the dimensions of which are adapted for its introduction into the mass spectrometer and which has a housing 9a or a plurality of housings 9a adapted for receiving the capture supports (optionally fitted into the aforementioned plate).

The measurement support advantageously has the shape of a plate and is made in an electrically conducting material.

Each housing 9a has a shape and dimensions substantially identical with those of the capture surface 1a (or, if necessary, with the outer shape of the plate 2), so that the capture support 1 and, if necessary the plate 2, are fitted into the measurement support, so as to ensure electric contact between the measurement support and the capture support.

FIG. 3B is a sectional view of the measurement support 9 in which a capture support 1 and the plate in which it is fitted are received into a housing 9a.

Preferably, the capture surface 1a is flush with the surface of the measurement support 9.

In a particularly advantageous way, the measurement support comprises 96 housings laid out so as to make the measurement support compatible with existing automated devices for treating the samples (notably for depositing the organic matrix) and for analysis.

Alternatively or additionally, analyses may be conducted by imaging, notably fluorescence imaging or colorimetry.

It is also possible to acquire images of scanning electron microscopy of the capture surface.

It is also possible to directly analyse the species captured by the capture surface by means of conventional histological techniques (staining, immune-marking) on fresh tissue, which cannot be carried out on a tissue sampled by conventional biopsy, for which it is necessary to set the tissue beforehand (for example by freezing, fixing and/or inclusion in paraffin) in order to generate histological sections.

Experimental Validations

A capture support in nanoporous silicon was tested by means of an ex vivo test consisting of depositing 10 µl of human cerebrospinal liquid directly on the capture surface.

Next, the surface was rinsed twice with an acid buffer (sodium acetate 100 mM, pH 4.0) for 1 minute. This rinsing gives the possibility of removing the species which have not adhered to the capture surface and/or impurities (tissue, blood residues, etc.). The surface was subsequently rinsed once again in water, and then it was dried in free air. An organic matrix (sinapinic acid for analysis of proteins, or CHCA (α-cyano-4-hydroxycinnamic acid) for analysis of peptides) was deposited on the capture surface, which was then subject to analysis by means of a commercial mass spectrometer SELDI (Biorad PCS 4000).

The readout parameters were adjusted depending on the mass scale of the species to be detected. The optimum conditions were determined manually on a few spots before launching automatic acquisition on 583 laser impacts regularly distributed for each sample:

for peptides (low molecular weight), an intensity of 1,000 nJ and an attenuation of the matrix signal at 500 Da were used, for proteins (high molecular weight), an intensity of 2,200 nJ and an attenuation of the matrix signal at 1,000 Da were used.

The same analysis was achieved as a comparison and with the same procedure by using as a capture support, a substrate holder of the type normally used in mass spectrometry, i.e. a smooth metal bar on which is deposited a polymer, the reference of which is Biorad CM10.

The results are represented in FIG. 4, where the upper graphs were obtained with the smooth reference substrate holder and the lower graphs with the capture support in nanoporous silicon.

As regards proteins (right-hand graph), it is observed that the "small" proteins are effectively bound on the capture surface of nanoporous silicon while the "large" proteins, and notably albumin are substantially removed.

The difference between both supports is even clearer in the case of peptides (left-hand graph: the latter are widely removed by rinsing in the case of the smooth support while in the case of the nanoporous capture support, a very rich spectrum is observed.

Another test was applied ex vivo for characterizing the capacity of the nanoporous capture support used in the invention of providing differentiated information depending on the sampling area on a same organ.

For this purpose, the sampling device comprising a capture support in nanoporous silicon was used for producing an extemporaneous imprint of a prostate tissue on a freshly excised part.

For this purpose, the fresh tissue was affixed on the capture surface, and the capture surface was then rinsed twice with 100% ethanol for 1 minute.

Next, the capture surface was rapidly rinsed in water and left to dry in free air.

An organic matrix (1 to 2 µl of CHCA) was deposited on the capture surface, and then a MALDI analysis was directly carried out on the capture surface.

The device used is a MALDI TOF/TOF Ultraflex Extreme equipment from Bruker, the parameters being: Laser energy comprised between 60 and 70%, attenuation of the matrix signal (Deflector) at 500 Da, in a linear mode.

Both graphs of FIG. 5 show the protein profiling (intensity versus the m/z ratio) obtained by MALDI spectrometry for two different areas of the prostate.

It is observed that the profiles are different from one area to the other, which shows that the capture support gives the possibility of accounting for the specificities of the tissues of two areas of a same organ.

Finally, it is obvious that the examples which have just been given are only particular illustrations, by no means limiting as to the fields of application of the invention, notably as regards the medical indications and the species to be analysed.

REFERENCES

WO 2006/082344

The invention claimed is:

1. A device for sampling biological material in vivo comprising:
    a capture support comprising a nanoporous material, said capture support having a nanoporous surface configured for capturing the biological material from living tissue,
    a plate that bears the capture support,
    a grasping rod, and
    a joint comprising a first member coupled with the grasping rod and a second member removably coupled with the plate bearing the capture support, so that the capture surface is selectively orientable relatively to the grasping rod, so as to adjust the orientation of the capture support relatively to the grasping rod.

2. The device according to claim 1, wherein the first and the second members of the joint may be separated so as to detach the capture support from the grasping rod.

3. The device according to claim 1, wherein the capture support is fitted into the plate, said plate having a rim flush with the capture surface, so that only the capture surface of said support is in contact with tissues during in vivo sampling.

4. The device according to claim 1, wherein the plate is in an electrically conducting material.

5. The device according to claim 1, wherein the joint is a ball joint.

6. The device according to claim 1, wherein the material of the capture support is nanoporous silicon.

7. The device according to claim 1, wherein the capture surface is circular and has a diameter of less than 10 mm.

8. The device according to claim 1, further comprising a device for orienting the capture support, comprising a cable extending along the grasping rod and coupled with the second member of the joint.

9. A device for sampling biological material in vivo comprising:
- a capture support comprising a nanoporous material, said capture support having a nanoporous surface configured for capturing the biological material from living tissue,
- a plate that bears the capture support, said plate being in an electrically conducting material,
- a grasping rod, and
- a joint comprising a first member coupled with the grasping rod and a second member removably coupled with the plate bearing the capture support, so that the capture surface is selectively orientable relatively to the grasping rod, so as to adjust the orientation of the capture support relatively to the grasping rod, wherein the tissue retains its histological structure.

10. A device for sampling biological material in vivo comprising:
- a capture support comprising a nanoporous material, said capture support having a nanoporous surface configured for capturing the biological material from living tissue,
- a plate that bears the capture support,
- a grasping rod, and
- a joint comprising a first member coupled with the grasping rod and a second member removably coupled with the plate bearing the capture support, so that the capture surface is selectively orientable relatively to the grasping rod, so as to adjust the orientation of the capture support relatively to the grasping rod,
- wherein the second member of the joint is coupled with the plate opposite the nanoporous surface of the capture support, wherein the tissue retains its histological structure.

11. The device of claim 1, wherein the tissue retains its histological structure.

* * * * *